United States Patent [19]
Barin

[11] Patent Number: 5,921,256
[45] Date of Patent: Jul. 13, 1999

[54] APPARATUS AND METHOD FOR CLEANING ELONGATED HOLLOW INSTRUMENTS

[75] Inventor: Michael Norris Barin, Asheville, N.C.

[73] Assignee: Charles J. DePaolo, Asheville, N.C.

[21] Appl. No.: 08/833,233

[22] Filed: Apr. 14, 1997

[51] Int. Cl.[6] .................................................. B08B 9/02
[52] U.S. Cl. .................................. 134/22.12; 134/22.18; 134/104.2; 134/166 C; 134/169 C; 134/95.2
[58] Field of Search ........................... 134/22.12, 22.18, 134/24, 104.2, 166 C, 169 C, 170, 95.2, 166 R; 422/292, 300

[56] References Cited

U.S. PATENT DOCUMENTS

| | | | |
|---|---|---|---|
| 1,400,797 | 12/1921 | Burnham | 134/170 |
| 1,861,768 | 6/1932 | Wappler . | |
| 2,671,742 | 3/1954 | Cozzoli | 134/170 |
| 3,040,755 | 6/1962 | Sidmon et al. . | |
| 3,537,897 | 11/1970 | Kington | 134/22.12 |
| 4,294,271 | 10/1981 | Intrater et al. . | |
| 4,299,244 | 11/1981 | Hirai . | |
| 4,337,223 | 6/1982 | Kaye . | |
| 4,354,514 | 10/1982 | Sundheimer et al. | 134/170 |
| 4,516,592 | 5/1985 | Schultz et al. . | |
| 4,552,728 | 11/1985 | Taylor | 134/166 R |
| 4,752,444 | 6/1988 | Bowen et al. . | |
| 5,078,164 | 1/1992 | Doellgast | 134/166 R |
| 5,279,317 | 1/1994 | Bowman et al. . | |
| 5,279,799 | 1/1994 | Moser . | |
| 5,310,524 | 5/1994 | Campbell et al. | 134/22.18 |
| 5,348,711 | 9/1994 | Johnson et al. | 134/170 |
| 5,505,218 | 4/1996 | Steinhauser et al. | 134/170 |
| 5,511,568 | 4/1996 | Bowman et al. . | |
| 5,554,228 | 9/1996 | Giordano et al. | 134/24 |
| 5,711,921 | 1/1998 | Langford | 134/170 |

FOREIGN PATENT DOCUMENTS

| | | | |
|---|---|---|---|
| 278194 | 5/1990 | Germany | 134/24 |
| 2-254184 | 10/1990 | Japan | 134/22.12 |
| 869859 | 10/1991 | Russian Federation | 134/24 |

*Primary Examiner*—Frankie L. Stinson
*Attorney, Agent, or Firm*—Carter & Schnedler, P.A.

[57] ABSTRACT

There is provided an apparatus and method for simultaneously cleaning a plurality of elongated hollow instruments, preferably surgical instruments, each of which has a first opening and a second opening. The apparatus includes a fixture for receiving the plurality of hollow instruments. The fixture includes a clamp for removably securing the instruments to the fixture. The fixture includes a hollow upright cylinder which is attached to a source of fluids. The upright cylinder is attached to a hollow manifold located below the clamp. The manifold includes a plurality of tubes extending therefrom which are adapted to be connected to the first openings in the instruments. Washing, rinsing and drying fluids pass through the fixture and through the instruments on a timed cycle so that the instruments may be cleaned simultaneously.

20 Claims, 6 Drawing Sheets

APPARATUS AND METHOD FOR CLEANING ELONGATED HOLLOW INSTRUMENTS

BACKGROUND OF THE INVENTION

This invention relates to apparatus for cleaning elongated hollow instruments. More particularly, it relates to apparatus for the simultaneous cleaning of a plurality of elongated hollow surgical instruments.

Endoscopic cannulated surgical instruments are slender elongated devices which include hollow tubes. Such instruments are used for various surgical procedures. The proximal end of the instrument includes a handle which may have finger receiving eyelets and the like for the surgeon to manipulate. The distal end of the instrument includes various surgical devices, such as cutting and suturing devices. Mechanical couplings in the hollow tube connect the surgical device at the distal end to the manipulating device at the proximal end.

The elongated instruments described above are being used more and more since endoscopic surgery has become popular.

One of the major problems in using these elongated hollow instruments is properly cleaning and disinfecting the instruments after use. Obviously, surgical instruments need to be thoroughly cleaned and properly sterilized between uses. Human tissue, blood and other bodily fluids often accumulate inside the hollow tube after the instrument is used. In addition, some hospitals and other medical facilities have been reusing certain elongated hollow instruments and other devices, such as hollow fiber artificial kidneys, which are designed to be disposable in order to save money.

There have been various scientific studies focused on the cleaning and sterilization of elongated surgical instruments. In an article by Geoffrey J. Gorse and Roberta L. Messner titled "Infection Control Practices in Gastrointestinal Endoscopy in the United States: A National Survey" which appeared in the October, 1991 issue of *Society of Gastroenterology Nurses and Associates*, a survey was reported on which ascertained the current infection control practices, endoscopic cleaning procedures, and perceive frisk of infection in connection with the reusable gastrointestinal endoscopic devices. Most of the respondents were hospitals. Significantly, this survey found that endoscopic related infections, usually bacterial, were reported to occur at 6% of the institution's responding.

Jean-Gaston DesCôteaux, Eric P. Poulen, Micheline sortie, Gilles Murray and Suzanne Gingras studied the rate of surgical complications relating to reuse of disposable laparoscopic instruments, with the results being published in *Canadian Journal of Surgery*, Volume 38, No. Dec. 6, 1995 in an article titled "Reuse of Disposable Laparoscopic Instruments: A Study of Related Surgical Complications". The study found that the combined rate for deep and superficial infections was 1.8%.

In an article appearing in the July, 1995 issue of the *AORN Journal*, Volume 62, No. 1, by DesCôteaux et al, titled "Residual Organic Debris on Processed Surgical Instruments", the investigators studied thirty-two laparoscopic instruments selected at random from the hospital's supply of processed surgical instruments. Visual inspection revealed that only twenty-nine of thirty-two of the laparoscopic instruments appeared to be clean. Microscopic examination using a photo micrographic system revealed residual debris on twenty-seven of thirty-two of the laparoscopic instruments.

There are various methods and apparatus for washing elongated surgical instruments taught in the patent literature. For example, U.S. Pat. No. 5,279,317 issued to Bowman et al teaches the cleaning of a single endoscopic cannulated instrument, i.e., one instrument is cleaned at a time.

There is a need for an inexpensive and easy to use apparatus for simultaneously cleaning a plurality of elongated surgical instruments.

OBJECTS OF THE INVENTION

It is therefore one object of this invention to provide an improved apparatus for cleaning a plurality of elongated hollow surgical instruments.

It is another object of this invention to provide an improved method for cleaning a plurality of elongated hollow surgical instruments.

It is still another object of this invention to provide an easy to use apparatus and method for cleaning a plurality of elongated hollow surgical instruments which will save time and money.

SUMMARY OF THE INVENTION

In accordance with one form of this invention, there is provided an apparatus for cleaning a plurality of elongated hollow instruments having first and second openings therein. The apparatus includes a mounting fixture for receiving the instruments. The fixture includes a clamp for removably securing the instruments to the fixture. A plurality of connection devices are provided, each for receiving at least one pressurized fluid. The connection devices are adapted to be connected to the first openings in the plurality of instruments so that the pressurized fluid will flow from the first openings of instruments to the second openings of instruments thereby cleaning the instruments. Preferably, the instruments are surgical instruments, such as laparoscopic instruments. It is preferred that three pressurized fluids are provided, namely, a solvent which is used as a cleaning fluid, a rinsing fluid and air. It is also preferred that a timing device be used which will cause the three fluids to flow through the surgical instruments in three discrete cycles. In addition, it is preferred that the fixture include an upright hollow cylinder which is attached to a connecter which, in turn, is attached to the source of fluids, and that a hollow manifold be attached to the hollow upright cylinder and that a plurality of tubes extend from the manifold to be connected to the first openings in the surgical instruments.

It is also preferred that the fixture include a container having a plurality of openings therein for receiving and securing the distal ends of the instruments thereto. In addition, it is preferred that the openings in the container include a plurality of resilient seals with the seals surrounding the distal ends of the instruments so that the fluid will flow from the first opening of the instruments into the container without becoming airborne prior to entering the container. The materials collected in the container may then be properly disposed of.

In accordance with another form of this invention, there is provided a method for cleaning a plurality of the elongated hollow instruments, each having first and second openings therein. The method includes removably securing the instruments to a fixture, attaching tubes to the first openings of the instruments, simultaneously applying a cleaning solution to the tubes, simultaneously applying a rinsing solution to the tubes, and then simultaneously applying air to the tubes so that the instruments are cleaned by the flow of the fluids through the hollow portions of the instruments in three timed cycles.

It is preferred that the method also include collecting residual materials from the tubes and the fluids in a container which is attached to the fixture and disposing of the residual materials and fluids.

BRIEF DESCRIPTION OF THE DRAWINGS

The subject matter which is regarded as the invention is set forth in the appended claims. The invention itself, however, together with further objects and advantages thereof may be better understood in reference to the accompanying drawings in which:

DESCRIPTION OF THE PREFERRED EMBODIMENT

Figure 1:
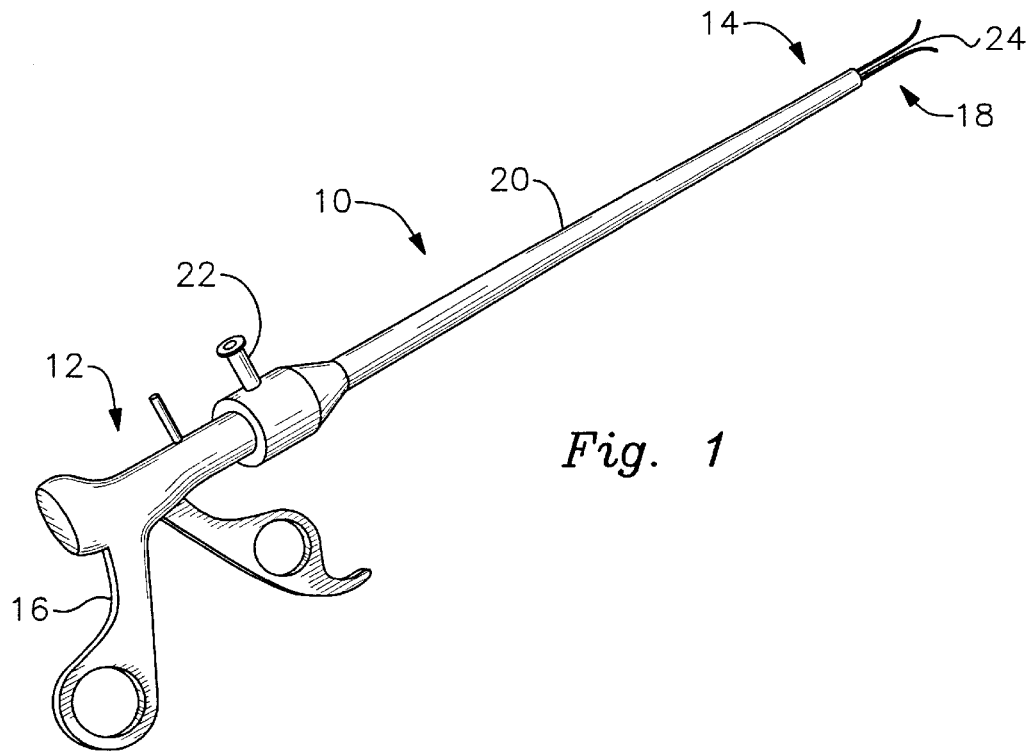
FIG. 1 is a pictorial view of a typical elongated surgical instrument to be cleaned in accordance with the teachings of this invention.

Referring now more particularly to FIG. 1, there is provided instrument 10 which is a typical elongated hollow surgical instrument which may be cleaned in accordance with the teachings of this invention. Instrument 10 includes proximal end 12 and distal end 14. Proximal end 12 includes control elements 15, such as grip handles 16 and 17. Distal end 14 includes surgical knifes 18, and may include a grasper or an electrical cautery (not shown). Instrument 10 includes elongated hollow tube 20 connecting proximal end 12 to distal end 14. Wires (not shown) may be received within elongated tube 20. The wires connect control elements 15 to knives 18 so that the surgeon may manipulate the control elements to cause the knifes 18 to perform a function.

Nipple 22 is connected to elongated hollow tube 20. The nipple forms a first opening in the instrument. A second opening 24 is provided at the distal end 14 of the instrument. Nipple 22 is normally used during surgery as a connecting post for saline.

Figure 2:
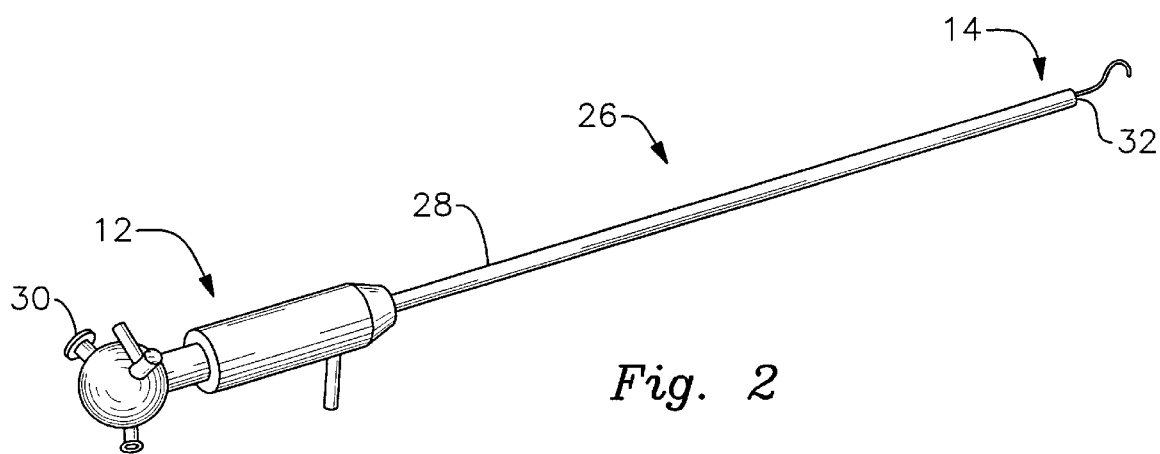
FIG. 2 is another typical elongated surgical instrument to be cleaned in accordance with teachings of this invention.

Referring now more particularly to FIG. 2, there is provided another laparoscopic instrument which also may be cleaned in accordance with the teachings of this invention. Instrument 26 includes elongated hollow tube 28 and nipple 30 attached thereto which forms a first opening at the proximal end 12. A second opening 32 is located at the distal end 14.

Figure 3:
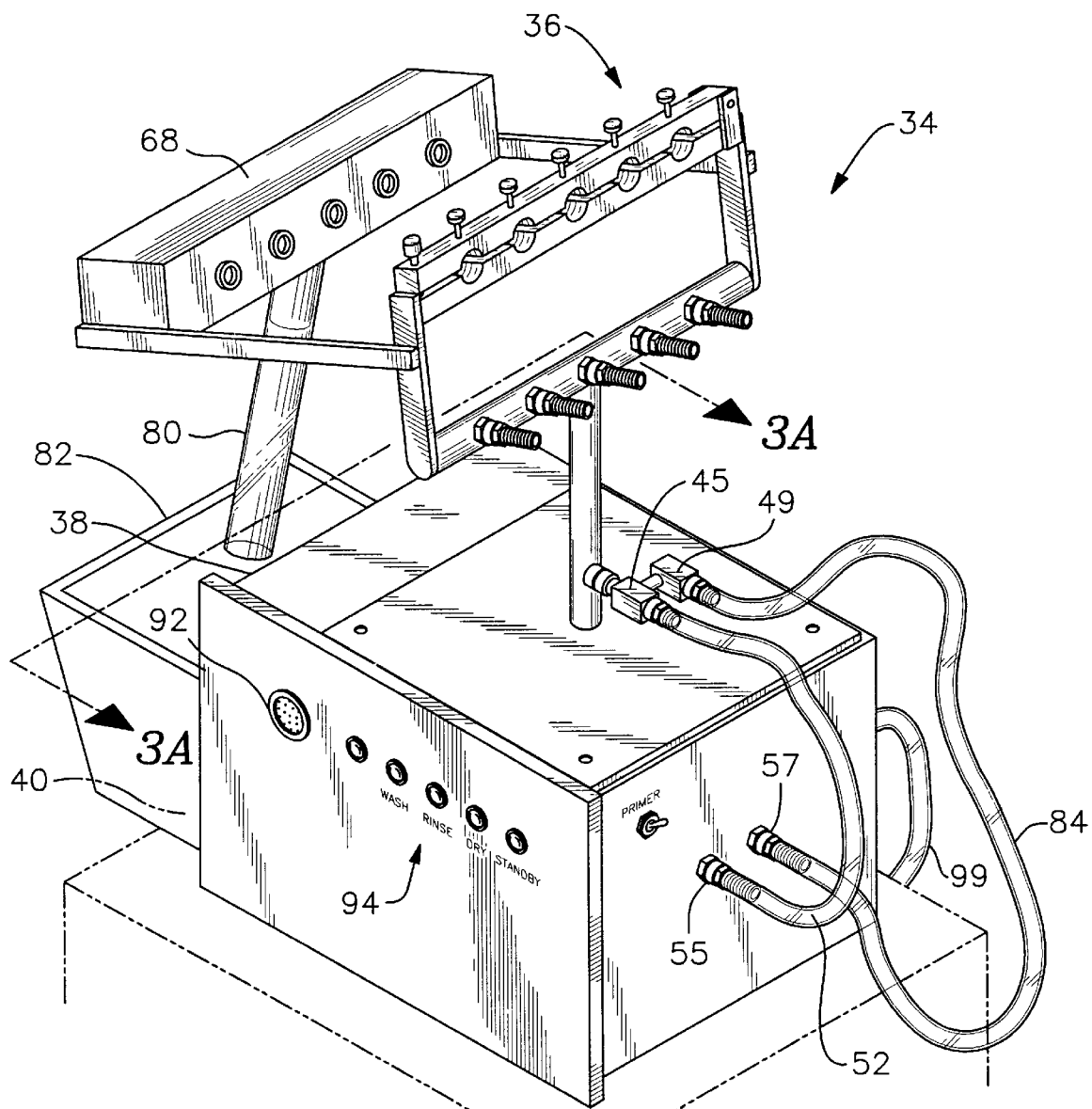
FIG. 3 is a pictorial view of the cleaning apparatus in accordance with this invention.
Figure 6:
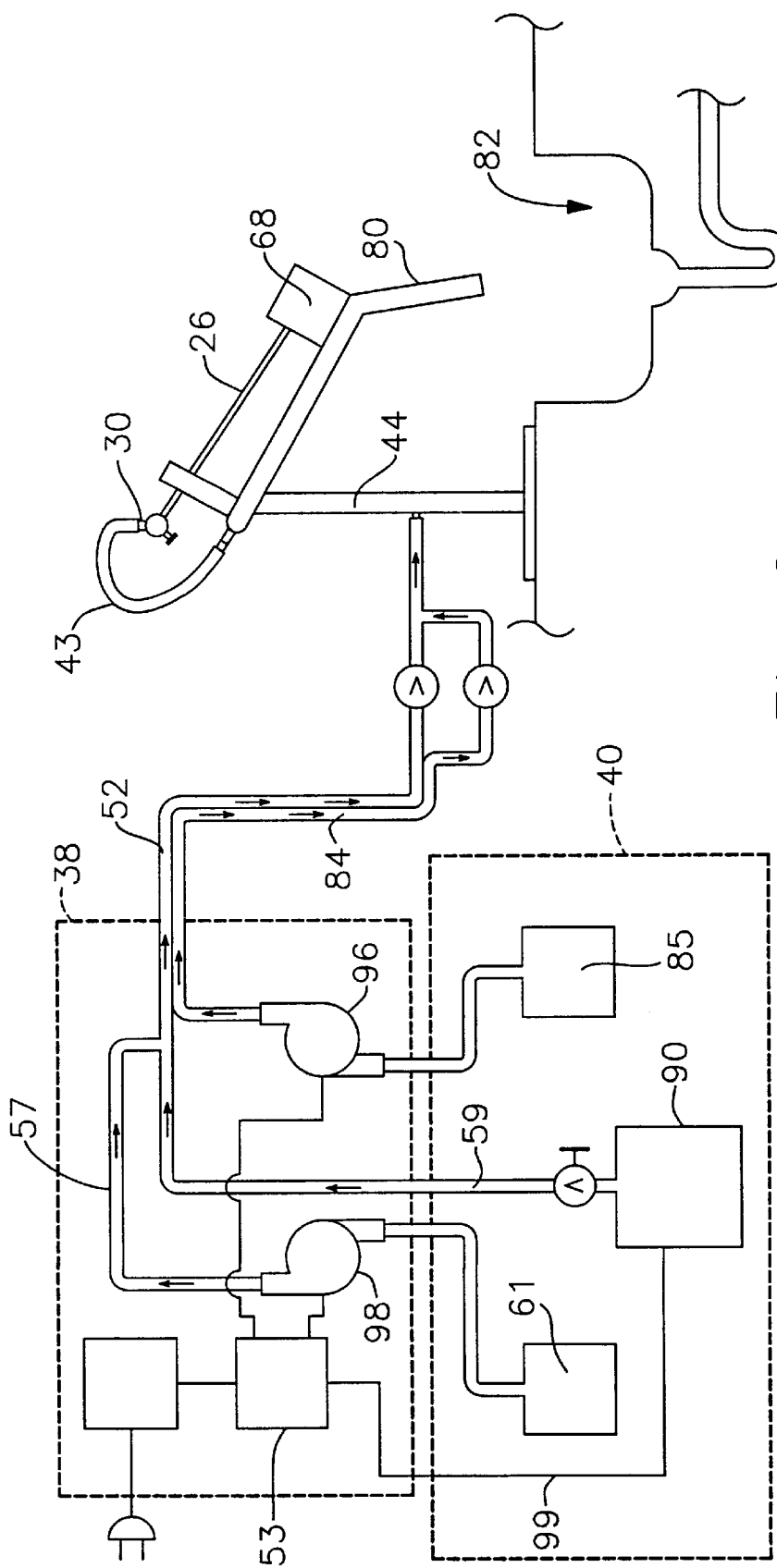
FIG. 6 is a side elevational view of the apparatus of the subject invention, with the side of the cabinet removed for clarity and with the cleaning fixtures removed from the top of the cabinet and placed adjacent to a sink.
Figure 7:
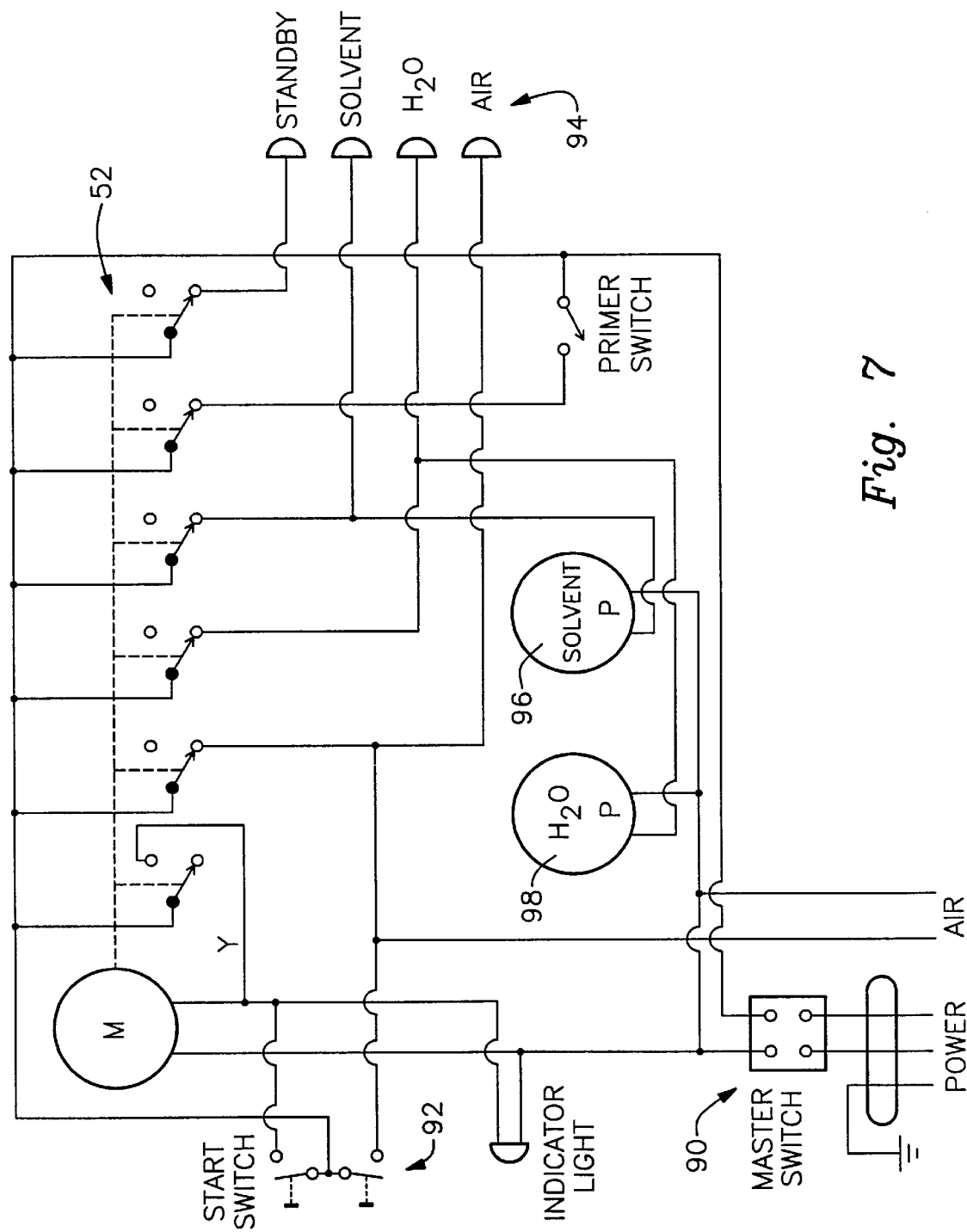
FIG. 7 is a detailed schematic diagram showing the details of the timing apparatus.

Referring now more particularly to FIG. 3, there is provided a cleaning apparatus 34 which includes fixture 36, housing 38 which receives fluid switching control apparatus and various pumps, and cabinet 40 which contains various fluid reservoirs and an air compressor, as will be described below in reference to FIGS. 6 and 7.

Figure 4:
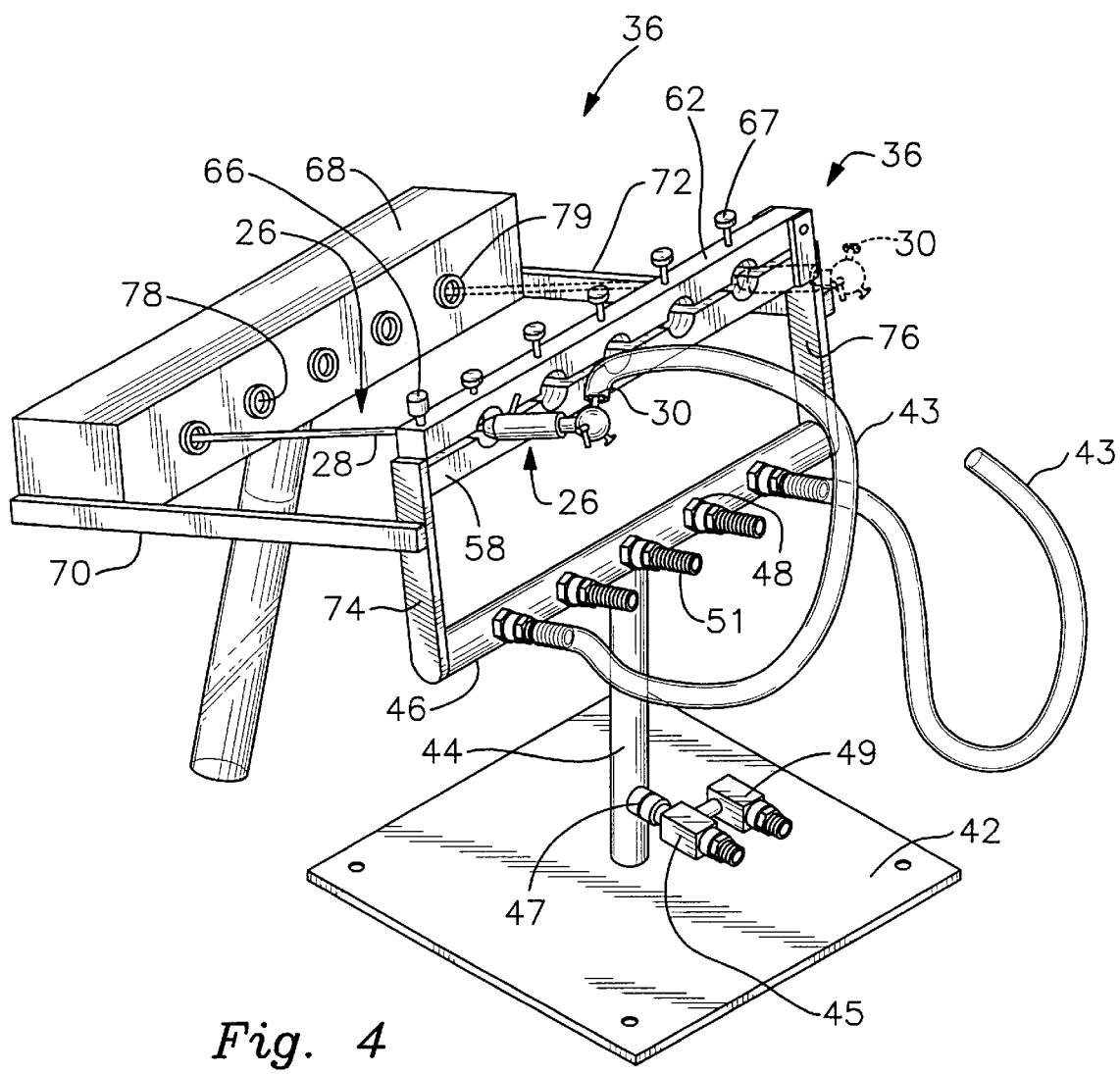
FIG. 4 is a pictorial view of the fixture portion of the apparatus of the subject invention having a plurality of elongated hollow surgical instruments secured thereto.

Referring now more particularly to FIG. 4, fixture 36 includes stand 42 to which hollow upright cylinder 44 is mounted. Hollow upright cylinder 44 is connected to hollow manifold 46. Hollow manifold 46 includes a plurality of openings 48 therein.

Figure 5:
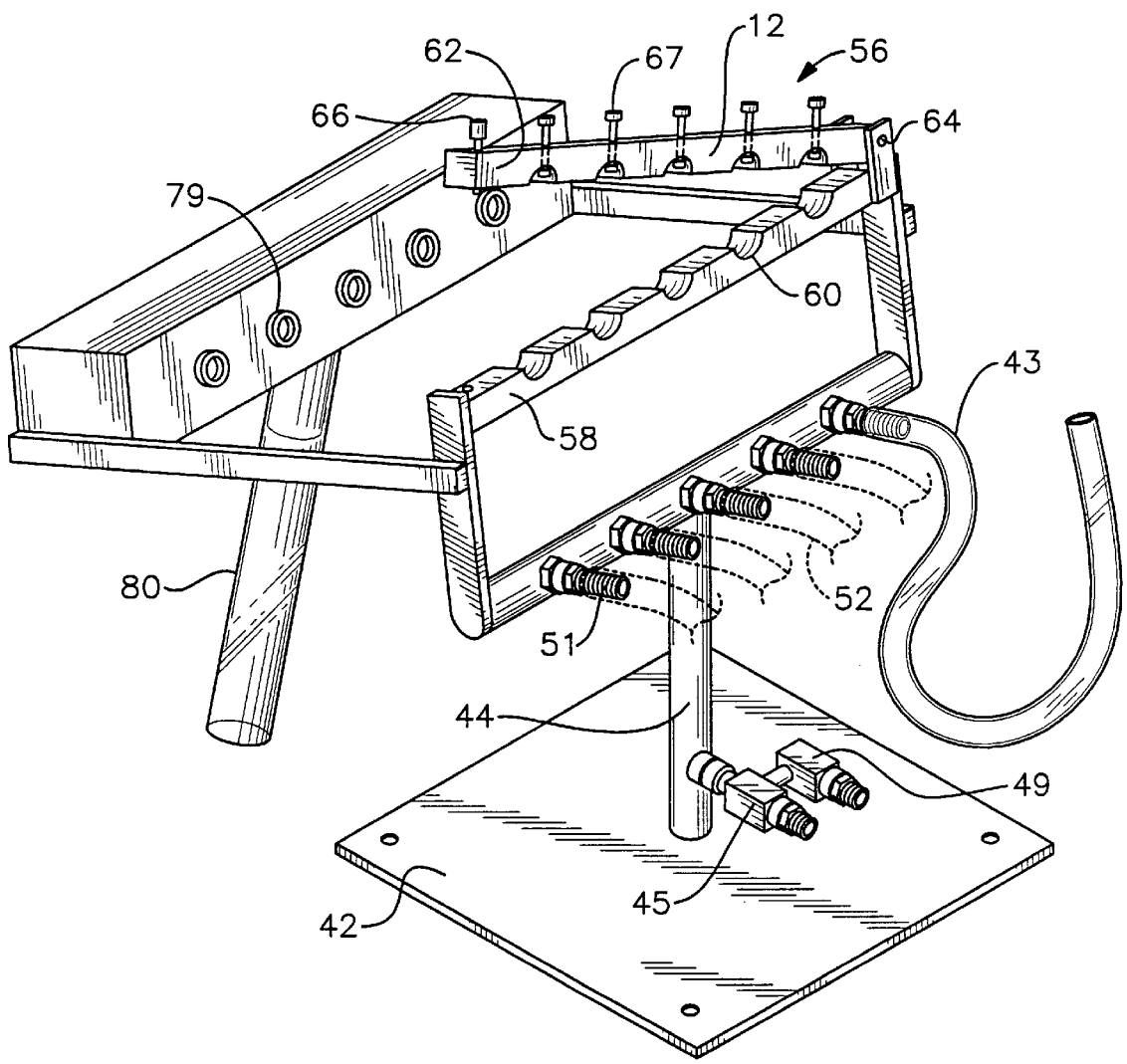
FIG. 5 is a pictorial view of the apparatus of FIG. 4, however, with the elongated hollow surgical instruments having been removed.

As better seen in FIG. 5, a plurality of hollow studs 51 extend from openings 48. Flexible tubes 52 are attached to the studs 51. Air/water connector 45 is attached to upright cylinder 44 through stud 47. Solvent connector 49 is attached to air/water connector 45. As can be seen in reference to FIG. 3, one end of tube 52 is attached to connector 45. The other end of tube 52 is connected to connector 55 which extends from housing 38 which contains the fluid switching and timing apparatus 53 shown in FIG. 7. Tube 84 is attached to connector 57 which extends from housing 38. Tube 84 carries solvent from the solvent reservoir 85 in cabinet 40 through pump 96 which is located in housing 38, as shown in FIG. 6. Tube 52 receives compressed air, and during the rinse cycle, receives water. One end of tube 52 is attached to connector 45. The other end of tube 52 is attached to connector 55. Tube 52, which is connected to the other side of connector 55 (not shown) on the inside of housing 38, is bifurcated into water tube 57 and air tube 59, as shown in FIG. 6. Water tube 57 passes through pump 98 and is connected to water reservoir 61. Air tube 59 is connected to a source of compressed air, such as an air compressor 90. Compressor 90 may be eliminated if compressed air is available from another source, such as from a wall connector.

Referring now to FIGS. 3, 4 and 5, fluid flows through stud 47 into hollow upright cylinder 44 through manifold 46 and out the openings 48 into tubes 43. This provides a fluid flow path through the hollow portion of fixture 36.

Referring now to FIGS. 4 and 5, elongated hollow surgical instruments, such as instrument 26, shown in FIG. 2, are secured to fixture 36. Fixture 36 includes clamp 56 which includes a lower fixed portion 58 having a plurality of grooves 60 therein and upper rotatable portion 62. Upper portion 62 is attached to lower portion 58 by means of hinge 64. A plurality of adjustable screws 67 are received through bore holes in upper portion 62. The screws 67 align with grooves 60 when clamp 56 is closed. The other end of the upper and lower portions are fixed together by screw 66. The hollow tube 28 of each instrument is removably secured to the fixture near the proximal end of the instrument by means of clamp 56. The rod portion of the instrument rests in a groove 60 and a corresponding screw 67 presses down on the top of each instrument to hold each instrument in place.

The preferred embodiment shows positions for five instruments, however, more or less than five instruments may be held in place for simultaneous washing. A container 68 is attached to the fixture 36 by means of brackets 70 and 72. Brackets 70 and 72, in turn, are attached to brackets 74 and 76 which are located between the lower portion 58 of the clamp 56 and manifold 46. Container 68 includes a plurality of holes 78 therein. Each hole receives a resilient seal 79. The distal end 14 of each surgical instrument is received in a hole 78 and is surrounded by the seal 79. The seals also help to secure the surgical instruments to the fixture. Drain pipe 80 is attached to the lower portion of the container 68. Drain pipe 80 is arranged such that it may be placed over a sink 82 which permits proper disposal of fluids and the like which accumulate in container 68.

As previously stated, it is preferred that the instruments be cleaned in an antegrade, i.e. proximal to distal, fashion by passing three fluids therethrough in timed cycles. Housing 38, as shown in FIGS. 3 and 6, contains the switching and timing apparatus and the pumps shown in FIGS. 6 and 7. Tube 84 carries the solvent, which acts as a cleaning fluid, and is connected through one side of housing 38. Tube 52 carries water for rinsing the instruments and air for drying the instruments. As shown in FIG. 7, the apparatus includes switching and timing apparatus 53, including timer 63. Start switch 92 is attached to the outside of housing 38. The four indicator lights 94 will inform the user of the status of the apparatus, namely, whether it is on standby, it is supplying leaning fluid, such as solvent, rinsing fluid, such as water, or drying fluid, such as air. Water reservoir 61, solvent reservoir 85 and a source of compressed air 90 are received within cabinet 40. An electrical control cable 99 connects the switching and timing apparatus 53 in housing 38 to the compressor 90 in cabinet 40. Electrical cables 101 and 103 connect the switching and timing apparatus 53 to pumps 96 and 98.

The instrument cleaning apparatus described above may be operated as set forth below. The upper rotatable portion 62 of clamp 56 is opened. A plurality of elongated hollow surgical instruments are placed between grooves 60 and a corresponding hole 78 in container 68. The clamp 56 is closed and secured by screw 66. Screws 67 are rotated clockwise so that their ends rest against the top surfaces of the instruments. Tubes 43 are attached to nipples 30, in the case of instruments shown in FIG. 2, and nipples 22, in the case of instruments shown in FIG. 1, which are located near the proximal end thereof. Any other openings in the proximal ends of the instrument are closed.

The operator presses the start switch, causing the switching and timing apparatus 53 to operate. Switching and timing apparatus 53 causes the air compressor 90 to come on, thereby providing air under high pressure to move through tube 52, connector 45 and stud 47, and at the same time switches on the pump 96 causing cleaning fluid or solvent to flow from tube 84 to connector 49 through stud 47 into hollow upright cylinder 44 and then into manifold 46. The solvent flows out manifold 46 through openings 48 and into connector tubes 43. The solvent, having increased its velocity due to the air flow through connector 45, then flows from connector tubes 43 through the hollow portion of the surgical instruments 26. The solvent and any residual matter, such as blood and tissue, are collected in container 68 and discharged from the container 68 through drain pipe 80 and into sink 82 for proper disposal. After the expiration of a predetermined period, as determined by the switching and timing apparatus 53, the solvent pump 96 is switched off and the switching and timing apparatus 53 causes the cleaning apparatus to go into the rinse cycle by turning on pump 98, thereby causing water to flow into tube 52 and to pass into connector 45. The water then travels the same route as the solvent, as set forth above, for a predetermined period of time. Upon the expiration of the time for rinse, the switching and timing apparatus switches off the water pump 98, thereby leaving on the air only, which is in tube 52. The air then flows in the same path as the solvent and the water, again, for a predetermined time as determined by the switching and timing apparatus so that the instruments are thoroughly dried. Thus the instruments, such as 22 and 26, are cleaned. The upper portion 62 of clamp 56 is rotated upwardly and the clean instruments are removed from the apparatus and are ready to be placed into a sterilizer.

Thus there is provided an apparatus and method for simultaneously cleaning a plurality of elongated hollow surgical instruments which is easy to use and inexpensive to operate. The apparatus may be made portable by applying four wheels to the bottom of cabinet 40 or may be operated by a wall mounted air supply, thereby eliminating the need for a compressor.

In addition, the invention may also be used to clean other hollow medical devices, such as hollow fiber artificial kidneys, by making minor modifications to the apparatus described above.

From the foregoing description of the preferred embodiment of the invention, it will be apparent that many modifications may be made therein. It will be understood, however, that the embodiment of the invention is an exemplification of the invention only and that the invention is not limited thereto. It is to be understood, therefore, that it is intended in the appended claims to cover all modifications as fall within the true spirit and scope of the invention.

I claim:

1. An apparatus for simultaneously cleaning a plurality of elongated hollow surgical instruments comprising:

a plurality of elongated hollow surgical instruments; each of said instruments having proximal and distal ends, and having an open nipple at the proximal end and an opening at the distal end;

a mounting fixture; said mounting fixture including a clamp securing said plurality of elongated hollow surgical instruments thereto;

said apparatus including a plurality of flexible tubes each adapted to be connected to said open nipple on an instrument; said flexible tubes connected to at least one source of fluid, whereby fluid from said flexible tubes will pass from said open nipple of each of said instruments through each instrument and out of said opening at said distal end for cleaning said instruments.

2. An apparatus as set forth in claim 1, wherein portions of said fixture are hollow; an opening in said hollow portion of said fixture for receiving fluid; said tubes connected to said hollow portion of said fixture, whereby the fluid may travel inside said hollow portion of said fixture through said tubes and through the instruments.

3. An apparatus as set forth in claim 2, wherein said hollow portion of said fixture includes an upwardly extending hollow member; a hollow manifold connected to said upwardly extending member; said upwardly extending member supporting the instruments in an elevated position and providing a conduit for fluid to flow into said manifold.

4. An apparatus as set forth in claim 3, wherein said manifold includes a plurality of openings; said plurality of openings respectively connected to said plurality of tubes.

5. An apparatus as set forth in claim 1, wherein said clamp includes an upper bar and a lower bar; said upper bar rotatably mounted to said lower bar; a portion of the instruments received between said upper and said lower bars.

6. An apparatus for cleaning a plurality of elongated hollow surgical instruments each having a first end and a second end, and each having a first opening at the first end and a second opening at the second end comprising:

a mounting fixture for receiving the plurality of elongated hollow instruments; said fixture including a single clamp for removably securing all of the plurality of instruments to said fixture by closing said clamp; said clamp comprising:

a fixed portion having a plurality of grooves therein for receiving the instruments, a rotatable portion having a plurality of grooves therein which align with said grooves in said fixed portion when said clamp is closed, and a hinge attaching said fixed portion to said rotatable portion;

a plurality of connection devices, each for receiving at least one pressurized fluid; said connection devices adapted to be connected to the first openings in the plurality of instruments, whereby said pressurized fluid will flow from the first opening through each instrument to the second opening, thereby cleaning the instruments.

7. An apparatus as set forth in claim 6, wherein fluid is simultaneously applied to each of the plurality of instruments.

8. An apparatus as set forth in claim 6, wherein said at least one fluid includes a solvent, a rinsing fluid and air.

9. An apparatus as set forth in claim 8, further including a switching and timing apparatus for causing the fluids to flow in cycles.

10. An apparatus as set forth in claim 6, wherein said clamp secures the instruments to said fixture near the first ends of the instruments; the instruments also being secured to said fixture near the second ends of the instruments.

11. An apparatus as set forth in claim 10, wherein said fixture includes a container; said container including a plurality of entry openings therein for receiving and securing the second ends of the instruments to said fixture.

12. An apparatus as set forth in claim 6, wherein a portion of said fixture is hollow; said hollow portion of said fixture being connected to a source of said pressurized fluid.

13. An apparatus as set forth in claim 12, wherein said connection device connect said hollow portion of said fixture to the first opening of the instruments; said connection device includes a plurality of tubes.

14. An apparatus as set forth in claim 13, wherein said hollow portion of said fixture includes an upright cylinder and a manifold; said upright cylinder connected to said manifold; said plurality of tubes attached to said manifold.

15. An apparatus as set forth in claim 6, further including a plurality of bore holes in said rotatable portion; each of said bore holes communicating with one of said plurality of grooves in said rotatable portion; each bore hole receiving an adjustable screw, whereby said adjustable screws may make contact with said instruments when said clamp is closed for firmly securing the instruments to the fixture.

16. An apparatus for cleaning a plurality of elongated hollow instruments each having a first end and a second end, and having first and second openings therein comprising:

a mounting fixture for receiving a plurality of elongated hollow instruments; said fixture including a clamp for removably securing the instruments to said fixture;

a plurality of connection devices, each for receiving at least one pressurized fluid, said connection devices each adapted to be connected to the first opening in the plurality of instruments, whereby said pressurized fluid will flow from the first opening of the instruments to the second opening of the instruments, thereby cleaning the instruments; said clamp secures the instruments to said fixture near the first ends of the instruments;

the instruments also being secured to said fixture near the second ends of the instruments; said fixture includes a container; said container including a plurality of entry openings therein for receiving and securing the second ends of the instruments to said fixture;

a plurality of resilient seals received in said entry openings of said container; said seals surrounding a portion of said second ends of the instruments, whereby fluids will flow from the first opening of the instruments into said container without becoming airborne prior to entry into said container.

17. An apparatus as set forth in claim 16, wherein said container includes at least one exit opening, whereby fluid may exit from said container for proper disposal.

18. A method for cleaning a plurality of elongated hollow surgical instruments having first and second ends, each having a first opening at said first end and a second opening at said second end comprising the steps of:

removably securing the plurality of instruments to a fixture by simultaneously clamping said instruments to said fixture using a single clamp for all of the plurality of instruments;

attaching tubes from said fixture to the first openings in the instruments;

simultaneously applying a cleaning solution to said tubes and to the hollow portion of said instruments;

simultaneously applying a rinsing solution to said tubes and to the hollow portion of said instruments;

simultaneously applying air to said tubes and to the hollow portion of said instruments, whereby the instruments are cleaned by the flow of the fluids from the first openings to the second openings through the hollow portions of the instruments in three timed cycles.

19. A method as set forth in claim 18, further including the step of collecting residual materials, including the cleaning fluids from the instruments, in a container which is attached to said fixture, whereby the fluids and residual materials may be disposed of.

20. An apparatus for cleaning a plurality of elongated hollow instruments each having a first end and a second end, and having first and second openings therein comprising:

a mounting fixture for receiving a plurality of elongated hollow instruments; said fixture including a clamp for removably securing the instruments to said fixture;

a plurality of connection devices, each for receiving at least one pressurized fluid, said connection devices each adapted to be connected to the first opening in the plurality of instruments, whereby said pressurized fluid will flow from the first opening of the instruments to the second opening of the instruments, thereby cleaning the instruments; said clamp secures the instruments to said fixture near the first ends of the instruments;

the instruments also being secured to said fixture near the second ends of the instruments; said fixture includes a container; said container including a plurality of entry openings therein for receiving and securing the second ends of the instruments to said fixture; said entry openings being of a size to tightly surround the instrument near its second end, whereby fluids will flow from the first opening of the instruments into said container without becoming airborne prior to entry into said container.

* * * * *